US008822559B2

(12) United States Patent
Zoller et al.

(10) Patent No.: US 8,822,559 B2
(45) Date of Patent: Sep. 2, 2014

(54) ELECTRON BEAM CURED SILICONE RELEASE MATERIALS

(75) Inventors: Panu K. Zoller, River Falls, WI (US); Jayshree Seth, Woodbury, MN (US); Timothy D. Filiatrault, Maplewood, MN (US); Junkang J. Liu, Woodbury, MN (US); Clayton A. George, Afton, MN (US); Zai-Ming Qiu, Woodbury, MN (US)

(73) Assignee: 3D Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/126,365

(22) PCT Filed: Oct. 29, 2009

(86) PCT No.: PCT/US2009/062608
§ 371 (c)(1),
(2), (4) Date: Jul. 14, 2011

(87) PCT Pub. No.: WO2010/056546
PCT Pub. Date: May 20, 2010

(65) Prior Publication Data
US 2011/0303120 A1    Dec. 15, 2011

Related U.S. Application Data

(60) Provisional application No. 61/109,211, filed on Oct. 29, 2008, provisional application No. 61/109,213, filed on Oct. 29, 2008.

(51) Int. Cl.
*C03C 25/10* (2006.01)
*C08G 18/67* (2006.01)
*C08F 2/46* (2006.01)
*C08J 3/28* (2006.01)
*A61L 24/04* (2006.01)
*C09J 183/04* (2006.01)
*C08L 83/04* (2006.01)
*A61L 15/58* (2006.01)

(52) U.S. Cl.
CPC ............ *A61L 24/043* (2013.01); *C08J 2383/04* (2013.01); *C09J 183/04* (2013.01); *C08L 83/04* (2013.01); *A61L 15/58* (2013.01); *C08J 3/28* (2013.01)
USPC .................. 522/91; 522/90; 522/1; 522/134; 522/150; 522/162; 522/113

(58) Field of Classification Search
USPC .................. 522/91, 90, 1, 134, 150, 162, 113
See application file for complete search history.

(56) References Cited

U.S. PATENT DOCUMENTS

| 991,574 A | 5/1911 | Wesson |
| 2,763,609 A | 9/1956 | Lewis |
| 2,956,904 A | 10/1960 | Hendricks |
| 3,146,799 A | 9/1964 | Frank |
| 4,201,808 A | 5/1980 | Cully |
| 4,348,454 A | 9/1982 | Eckberg |
| 4,547,431 A | 10/1985 | Eckberg |
| 4,684,670 A | 8/1987 | Eckberg |
| 4,767,494 A | 8/1988 | Kobayashi |
| 4,810,728 A | 3/1989 | Gross |
| 4,859,712 A | 8/1989 | Cox |
| 4,865,920 A | 9/1989 | Sweet |
| 4,991,574 A | 2/1991 | Pocknell |
| 5,147,916 A | 9/1992 | Sweet |
| 5,162,410 A | 11/1992 | Sweet |
| 5,248,739 A | 9/1993 | Schmidt |
| 5,302,671 A | 4/1994 | Cifuentes |
| 5,356,940 A | 10/1994 | Giesen |
| 5,436,274 A | 7/1995 | Sumpter |
| 5,543,231 A | 8/1996 | Kidon |
| 5,661,192 A | 8/1997 | Giraud |
| 5,670,555 A | 9/1997 | Loiselle |
| 5,683,527 A | 11/1997 | Angell |
| 5,747,172 A | 5/1998 | Crivello |
| 5,804,610 A | 9/1998 | Hamer |
| 5,905,123 A | 5/1999 | Cifuentes |
| 5,907,018 A | 5/1999 | Mazurek |
| 5,961,770 A | 10/1999 | Cifuentes |
| 6,051,747 A | 4/2000 | Lindqvist |
| 6,207,875 B1 | 3/2001 | Lindqvist |
| 6,359,026 B1 | 3/2002 | Marquardt |
| 6,406,793 B1 | 6/2002 | Aoki |
| 6,472,581 B1 | 10/2002 | Muramatsu |
| 6,545,086 B1 | 4/2003 | Kosal |
| 6,664,359 B1 | 12/2003 | Kangas |

(Continued)

FOREIGN PATENT DOCUMENTS

| CN | 1813022 | 8/2006 |
| EP | 452034 | 10/1991 |
| EP | 2062952 | 5/2009 |
| GB | 805388 | 12/1958 |
| GB | 818987 | 8/1959 |
| JP | 62-149308 | 7/1987 |
| JP | 5169595 | 7/1993 |
| JP | 11140323 | 5/1999 |
| WO | WO 95-23694 | 9/1995 |
| WO | WO 96-35458 | 11/1996 |

(Continued)

OTHER PUBLICATIONS

ASTM D 3330M-90 Standard Test Methods for Peel Adhesion of Pressure-Sensitive Tape at 180 Angle [Metric]1, pp. 464-467.
ASTM E 1818-96[e1], Standard Practice for Dosimetry in an Electron Beam Facility for Radiation Processing at Energies Between 80 and 300 keV[1], 1996, pp. 903-910.

(Continued)

*Primary Examiner* — Ling Choi
*Assistant Examiner* — Jessica E Whiteley
(74) *Attorney, Agent, or Firm* — Dean M. Ehrich

(57) ABSTRACT

Methods of electron beam curing nonfunctional polysiloxanes and silanol terminated polysiloxanes are described. The resulting release materials are also described.

8 Claims, 1 Drawing Sheet

(56) References Cited

U.S. PATENT DOCUMENTS

| | | |
|---|---|---|
| 6,818,673 B2 | 11/2004 | Ferguson |
| 6,846,508 B1 | 1/2005 | Colas |
| 6,890,601 B2 | 5/2005 | Griswold |
| 7,005,475 B2 | 2/2006 | Griswold |
| 7,371,464 B2 | 5/2008 | Sherman |
| 7,393,879 B1 | 7/2008 | Kresta |
| 7,407,709 B2 | 8/2008 | Zhou |
| 2001/0037008 A1 | 11/2001 | Sherman |
| 2002/0013442 A1 | 1/2002 | Sherman |
| 2005/0113479 A1 | 5/2005 | Eckberg |
| 2005/0136266 A1 | 6/2005 | Zhou |
| 2005/0282024 A1 | 12/2005 | Sherman |
| 2007/0110941 A1 | 5/2007 | Utesch |
| 2007/0202245 A1 | 8/2007 | Gantner |
| 2007/0212314 A1 | 9/2007 | Murphy |
| 2008/0058460 A1 | 3/2008 | Tonge |
| 2009/0117310 A1 | 5/2009 | Ellringmann |
| 2010/0310852 A1 | 12/2010 | Weidinger |
| 2011/0206923 A1 | 8/2011 | Liu |
| 2011/0206924 A1 | 8/2011 | Liu |

FOREIGN PATENT DOCUMENTS

| | | | |
|---|---|---|---|
| WO | WO 98-23305 | 6/1998 | |
| WO | WO 99-18166 | 4/1999 | |
| WO | WO 02-097003 | 12/2002 | |
| WO | WO 03-010257 | 2/2003 | |
| WO | WO 2005-005705 | 1/2005 | |
| WO | WO 2005/063890 | * 7/2005 | ............. C08L 83/04 |
| WO | WO 2008-027498 | 3/2008 | |
| WO | WO 2008-057155 | 5/2008 | |
| WO | WO 2009-076389 | 6/2009 | |
| WO | WO 2010-056544 | 5/2010 | |
| WO | WO 2011-136977 | 11/2011 | |

OTHER PUBLICATIONS

Frounchi,"Comparison Between Electron-beam and Chemical Crosslinking of Silicone Rubber", Nuclear Instruments and Methods in Physics Research B, 2006, vol. 243, pp. 354-358.

Labouriau, "Mössbauer, NMR and ATR-FTIR spectroscopic investigation of degradation in RTV siloxane foams," Polym. Degradation & Stability, 2007, vol. 92, pp. 414-424.

Lin, "Recent advances in silicone pressure-sensitive adhesives," J. Adhesion Sci. Technol., Feb. 2007,vol. 21, No. 7, pp. 605-623.

Park, "Mechanical Properties and Antibacterial Activity of Peroxide-Cured Silicone Rubber Foams," J. Appl. Polym. Sci, May 2008, vol. 110, pp. 1723-1729.

International Search Report for PCT/US2009/062563, Feb. 12, 2010, 3 pages.

International Search Report for PCT/US2009/062576, Feb. 9, 2010, 4 pages.

International Search Report for PCT/US2009/062608, Feb. 8, 2010, 3 pages.

International Search Report for PCT/US2011/033021, mailed Jul. 11, 2011, 3 page.

International Search Report for PCT/US2009/062603, Feb. 9, 2010, 3 pages.

* cited by examiner

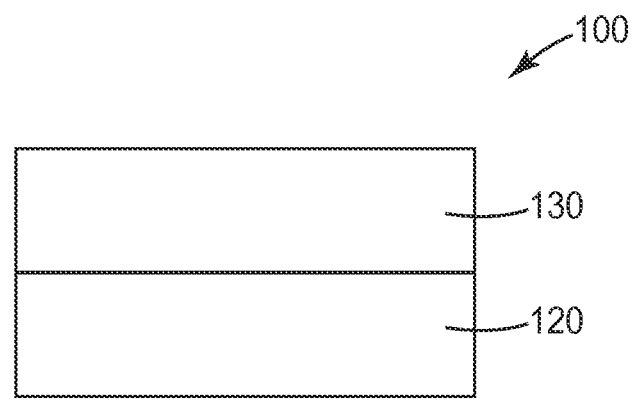

US 8,822,559 B2

ELECTRON BEAM CURED SILICONE RELEASE MATERIALS

CROSS REFERENCE TO RELATED APPLICATIONS

This application is a national stage filing under 35 U.S.C. 371 of PCT/US2009/062608, filed Oct. 29, 2009, which claims priority to U.S. Provisional Application Nos. 61/109,211 and 61/109,213, both filed Oct. 29, 2008, the disclosure of which is incorporated by reference in their entirety herein.

FIELD

The present disclosure relates to silicone release materials and release liners incorporating such release materials. In particular, the present disclosure relates to electron beam cured polysiloxanes, including low molecular weight polysiloxane fluids.

SUMMARY

Briefly, in one aspect, the present disclosure provides a method of making a silicone release layer. The methods include applying a composition comprising a polysiloxane material on a substrate and electron beam curing the composition to crosslink the polysiloxane material.

In some embodiments, the polysiloxane material consists essentially of one or more polysiloxane fluids having a kinematic viscosity at 25° C. of no greater than 50,000 centistokes, e.g., between 5,000 and 50,000 centistokes. In some embodiments, the polysiloxane material comprises a poly dimethylsiloxane. In some embodiments, all polysiloxane materials in the composition are nonfunctional polysiloxanes. In some embodiments, each nonfunctional polysiloxane is a polysiloxane fluid having a kinematic viscosity at 25° C. of no greater than 50,000 centistokes, e.g., between 5,000 and 50,000 centistokes.

In some embodiments, the polysiloxane material comprises a silanol terminated polysiloxane fluid having a kinematic viscosity at 25° C. of no greater than 50,000 centistokes, e.g., between 5,000 and 50,000 centistokes. In some embodiments, each polysiloxane material in the composition is independently selected from the group consisting of nonfunctional polysiloxanes, silanol terminated polysiloxanes, and alkoxy terminated polysiloxanes.

In some embodiments, the composition is substantially free of catalysts and initiators. In some embodiments, the composition comprises no greater than 5 wt. % solvent.

In another aspect, the present disclosure provides a release coated substrate made according to any of the various methods of the present disclosure. In some embodiments, the electron beam cured composition comprises a polysiloxane fluid having a kinematic viscosity at 25 of no greater than 50,000 centistokes, e.g., between 5,000 and 50,000 centistokes that has been crosslinked. In some embodiments, the composition consists essentially of one or more nonfunctional polysiloxane fluids, each having a kinematic viscosity at 25° C. of no greater than 50,000 centistokes, e.g., between 5,000 and 50,000 centistokes, wherein the polysiloxane fluids have been crosslinked. In some embodiments, the composition comprises a silanol terminated polysiloxane fluid having a kinematic viscosity at 25° C. of no greater than 50,000 centistokes, e.g., between 5,000 and 50,000 centistokes that has been crosslinked. In some embodiments, the composition is substantially free of catalysts and initiators.

The above summary of the present disclosure is not intended to describe each embodiment of the present invention. The details of one or more embodiments of the invention are also set forth in the description below. Other features, objects, and advantages of the invention will be apparent from the description and from the claims.

BRIEF DESCRIPTION OF THE DRAWINGS

FIG. 1 illustrates an exemplary release liner according to some embodiments of the present disclosure.

DETAILED DESCRIPTION

Pressure sensitive adhesives (PSAs) are an important class of materials. Generally, PSAs adhere to a substrate with light pressure (e.g., finger pressure) and typically do not require any post-curing (e.g., heat or radiation) to achieve their maximum bond strength. A wide variety of PSA chemistries are available including, e.g., acrylic, rubber, and silicone based systems.

Adhesives, including PSAs are often used as free films or as supported films, e.g., single- and double-coated tapes. Often, release liners are used to protective the adhesive layer during handling (e.g., processing, shipping, storing, and converting) and use (e.g., application to a substrate). Release liners typically comprise a substrate coated with a release material. In use, the release liner is removed from the adhesive layer, exposing the adhesive layer so that it may adhered to the desired target substrate. In such applications, the release liner may be reused, but is frequently discarded. In some applications, an adhesive article may be self-wound. In such cases, a substrate is coated on one side with a release material, with the adhesive bonded to the opposite side of the substrate. When the article is wound upon itself (i.e., self wound), the exposed adhesive surface comes in contact with the release coated side of the substrate. In use, the roll is unwound, and the adhesive is applied to the desired target substrate.

Crosslinked silicones have been used as release materials. Conventional silicone release materials are cured by thermal processes using specific types of catalysts. For example, platinum catalysts have been used with addition cure systems, peroxides (e.g., benzoyl peroxide) have been used with hydrogen-abstraction cure systems, and tin catalysts have been used with moisture/condensation cure systems.

Generally, these approaches require reactive functional groups attached to the siloxane backbone. For example, addition-cure, platinum-catalyzed systems generally rely on a hydrosilation reaction between silicon-bonded vinyl functional groups and silicon-bonded hydrogens. In general, it may be desirable to have a silicone release system that can be cured without the use of catalysts. It can also be useful to provide release coatings that do not require specific functional groups for proper curing.

UV-cured and electron-beam cured silicone release materials have been used. These systems require the use of catalysts and specific functional groups. In particular, acrylate-functional and epoxy-functional silicones have been radiation cured in the presence of catalysts.

The present inventors have discovered new methods for producing release layers, and release articles comprising such release layers. Generally, the methods include electron beam curing silicone materials to form a crosslinked polysiloxane network. Generally, the methods can be used with non-functional silicone materials. Functional silicone materials may also be used; however, as the specific functional groups are not typically involved in the crosslinking, the nature and presence of these functional groups is not critical.

In contrast to previous methods for curing silicone materials, the methods of the present disclosure do not require the use of catalysts or initiators. Thus, the methods of the present disclosure can be used to cure compositions that are "substantially free" of such catalysts or initiators. As used herein, a composition is "substantially free of catalysts and initiators" if the composition does not include an "effective amount" of a catalyst or initiator. As is well understood, an "effective amount" of a catalyst or initiator depends on a variety of factors including the type of catalyst or initiator, the composition of the curable material, and the curing method (e.g., thermal cure, UV-cure, and the like). In some embodiments, a particular catalyst or initiator is not present at an "effective amount" if the amount of catalyst or initiator does not reduce the cure time of the composition by at least 10% relative to the cure time for same composition at the same curing conditions, absent that catalyst or initiator.

Generally, the silicone materials useful in the present disclosure are polysiloxanes, i.e., materials comprising a polysiloxane backbone. In some embodiments, the nonfunctionalized silicone materials can be a linear material described by the following formula illustrating a siloxane backbone with aliphatic and/or aromatic substituents:

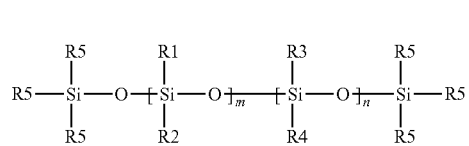

(1)

wherein R1, R2, R3, and R4 are independently selected from the group consisting of an alkyl group and an aryl group, each R5 is an alkyl group and n and m are integers, and at least one of m or n is not zero. In some embodiments, one or more of the alkyl or aryl groups may contain a halogen substituent, e.g., fluorine. For example, in some embodiments, one or more of the alkyl groups may be —CH$_2$CH$_2$C$_4$F$_9$.

In some embodiments, R5 is a methyl group, i.e., the nonfunctionalized polysiloxane material is terminated by trimethylsiloxy groups. In some embodiments, R1 and R2 are alkyl groups and n is zero, i.e., the material is a poly(dialkylsiloxane). In some embodiments, the alkyl group is a methyl group, i.e., poly(dimethylsiloxane) ("PDMS"). In some embodiments, R1 is an alkyl group, R2 is an aryl group, and n is zero, i.e., the material is a poly(alkylarylsiloxane). In some embodiments, R1 is methyl group and R2 is a phenyl group, i.e., the material is poly(methylphenylsiloxane). In some embodiments, R1 and R2 are alkyl groups and R3 and R4 are aryl groups, i.e., the material is a poly(dialkyldiarylsiloxane). In some embodiments, R1 and R2 are methyl groups, and R3 and R4 are phenyl groups, i.e., the material is poly(dimethyldiphenylsiloxane).

In some embodiments, the nonfunctionalized polysiloxane materials may be branched. For example, one or more of the R1, R2, R3, and/or R4 groups may be a linear or branched siloxane with alkyl or aryl (including halogenated alkyl or aryl) substituents and terminal R5 groups.

As used herein, "nonfunctional groups" are either alkyl or aryl groups consisting of carbon, hydrogen, and in some embodiments, halogen (e.g., fluorine) atoms. As used herein, a "nonfunctionalized polysiloxane material" is one in which the R1, R2, R3, R4, and R5 groups are nonfunctional groups.

Generally, functional silicone systems include specific reactive groups attached to the polysiloxane backbone of the starting material (for example, hydroxyl and alkoxy groups). As used herein, a "functionalized polysiloxane material" is one in which at least one of the R-groups of Formula 2 is a functional group.

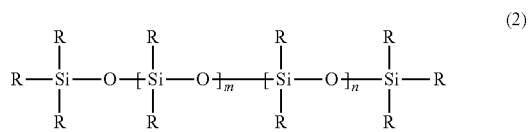

(2)

In some embodiments, a functional polysiloxane material is one is which at least 2 of the R-groups are functional groups. Generally, the R-groups of Formula 2 may be independently selected. In some embodiments, all functional groups are hydroxy groups and/or alkoxy groups. In some embodiments, the functional polysiloxane is a silanol terminated polysiloxane, e.g., a silanol terminated poly dimethylsiloxane. In some embodiments, the functional silicone is an alkoxy terminated poly dimethyl siloxane, e.g., trimethyl siloxy terminated poly dimethyl siloxane.

In addition to functional R-groups, the R-groups may be nonfunctional groups, e.g., alkyl or aryl groups, including halogenated (e.g., fluorinated) alky and aryl groups. In some embodiments, the functionalized polysiloxane materials may be branched. For example, one or more of the R groups may be a linear or branched siloxane with functional and/or nonfunctional substituents.

Generally, the silicone materials may be oils, fluids, gums, elastomers, or resins, e.g., friable solid resins. Generally, lower molecular weight, lower viscosity materials are referred to as fluids or oils, while higher molecular weight, higher viscosity materials are referred to as gums; however, there is no sharp distinction between these terms. Elastomers and resins have even higher molecular weights that gums, and typically do not flow. As used herein, the terms "fluid" and "oil" refer to materials having a dynamic viscosity at 25° C. of no greater than 1,000,000 mPa·sec (e.g., less than 600,000 mPa·sec), while materials having a dynamic viscosity at 25° C. of greater than 1,000,000 mPa·sec (e.g., at least 10,000,000 mPa·sec) are referred to as "gums".

In order to obtain the low thicknesses generally desirable for release material, it is often necessary to dilute high molecular weight materials with solvents in order to coat or otherwise apply them to a substrate. In some embodiments, it may be preferable to use low molecular weight silicone oils or fluids, including those having a dynamic viscosity at 25° C. of no greater than 200,000 mPa·sec, no greater than 100,000 mPa·sec, or even no greater than 50,000 mPa·sec.

In some embodiments, it may be useful to use materials compatible with common solventless coating operations, including, e.g., those having a kinematic viscosity at 25° C. of no greater than 50,000 centistokes (cSt), e.g., no greater than 40,000 cSt, or even no greater than 20,000 cSt. In some embodiments, it may be desirable to use a combination of silicone materials, wherein at least one of the silicone materials has a kinematic viscosity at 25° C. of at least 5,000 centistokes (cSt), e.g., at least 10,000 cSt, or even at least 15,000 cSt. In some embodiments, it may be desirable to use silicone materials having a kinematic viscosity at 25° C. of between 1000 and 50,000 cSt, e.g., between 5,000 and 50,000 cSt, or even between 10,000 and 50,000 cSt

EXAMPLES

A commercially available was used to evaluate the release and readhesion properties associated with the various electron beam cured release coating. The adhesive (ADH) was a crosslinked acrylic copolymer. ADH is available as a 51 micrometer (2 mil) thick transfer tape under the trade designation 467MP from 3M Company.

Non-functional Silicone Materials. The following examples were prepared by electron beam curing non-functional silicone materials. Coating materials were prepared by dissolving DC-200 silicone fluid (30,000 cSt, from Dow Chemical Company) in heptane to produce a 30 wt. % solids solution. This coating was applied with a flat stiff blade at 70 kPa (10 psi) pressure onto a polycoated kraft paper substrate (58# PCK from Jencoat). The samples were dried at room temperature. The resulting samples had a dry coat weight of 0.6 to 0.8 gram/square meter (0.14 to 0.20 grains per four inch by six inch sample).

The nonfunctional silicone material was electron beam cured according to the following procedure. The samples were cured using an acceleration voltage of 280 keV at various dosage levels.

E-Beam Curing Procedure. E-beam curing was performed on a Model CB-300 electron beam generating apparatus (available from Energy Sciences, Inc. (Wilmington, Mass.). Generally, a support film (e.g., polyester terephthalate support film) was run through the inerted chamber of the apparatus. Samples of uncured material were attached to the support film and conveyed at a fixed speed of about 6.1 meters/min (20 feet/min) through the inerted chamber and exposed to electron beam irradiation. For e-beam dosages of less than 18 Mrad, a single pass through the e-beam chamber was sufficient. To obtain higher dosages, e.g., 18 and 20 Mrad, two passes were required.

Adhesives applied to the cured release surface using both a "Dry Lamination" and "Wet-Cast" procedure. For the Dry Lamination samples, a 50 micron (2.0 mil) primed PET film (product 3SAB from Mitsubishi) was adhered to the transfer adhesive and pulled off to create the test samples. The adhesive side of the tape was then dry laminated onto the cured silicone coating of each sample using two passes of a 2 kg rubber roller. For the Wet Cast samples, the adhesives were cast directly on the cured silicone coatings of the examples and cured with ultraviolet radiation. A 50 micron (2.0 mil) primed PET film (product 3SAB from Mitsubishi) was then laminated to the cured adhesive to form the test samples.

Release Test Procedure. The PET-backed tape samples were peeled from the liner at an angle of 180° and at a rate of 230 cm/min (90 inches/minute). An IMass model SP2000 peel tester obtained from IMASS, Inc., Accord, Mass., was used to record the peel force.

Readhesion Test Procedure. To determine the readhesion value, the PET-backed tape samples were peeled from the liner using the Release Test method and the tape was then applied to the surface of a clean stainless steel panel. The tape sample was rolled down against the panel by means of two passes (forward and back) with a 2 kg rubber roller at 61 cm/min (24 inches/min). The readhesion value was a measure of the force required to pull the tape from the steel surface at an angle of 180° at a rate of 30.5 cm/min (12 inches/minute). The IMass model SP2000 peel tester was used to record the peel force.

The electron beam dose, liner release and readhesion for the dry-laminated samples are summarized in Table 1A. Similarly, the electron beam dose, liner release and readhesion for the wet-cast samples are summarized in Table 1B. The release and readhesion were measured initially and after a five day dwell of the adhesive against the release coating at 90° C. and 90% relative humidity (90/90).

TABLE 1A

Release and readhesion results for dry laminated samples.

| | | | Initial (gm/2.54 cm) | | 90/90 (gm/2.54 cm) | |
|---|---|---|---|---|---|---|
| Ex. | Adh. | Dose (Mrad) | Release | Readhesion | Release | Readhesion |
| 1 | ADH | 14 | 21.7 | 1000 | 25.1 | 970 |
| 2 | ADH | 16 | 21.2 | 1040 | 27.9 | 1160 |
| 3 | ADH | 18 | 23.9 | 940 | 36.0 | 880 |
| 4 | ADH | 20 | 18.3 | 1040 | 20.8 | 1080 |

TABLE 1B

Release and readhesion results for wet cast samples.

| | | | Initial (gm/2.54 cm) | | 90/90 (gm/2.54 cm) | |
|---|---|---|---|---|---|---|
| Ex. | Adh. | Dose (Mrad) | Release | Readhesion | Release | Readhesion |
| 1 | ADH | 14 | 42.0 | 820 | 80.9 | 1000 |
| 2 | ADH | 16 | 44.6 | 900 | 43.8 | 1120 |
| 3 | ADH | 18 | 46.6 | 1060 | 49.1 | 1210 |
| 4 | ADH | 20 | 44.8 | 1170 | 45.9 | 1370 |

Functional Silicone Materials. The following samples were prepared by electron beam curing a silanol terminated functional silicone fluid. Silanol terminated polydimethyl siloxane (DMS-542, 18,000 cSt, from Gelest) was coated with a flat, stiff blade to a coat weight of 1.3 to 2.3 gram/square meter on a 115 micron (4.5 mil) thick polyethylene liner, which had been nitrogen corona treated at 0.71 Joule per square centimeter. The coated samples were electron beam cured in an inert atmosphere (less than 50 ppm oxygen) using an acceleration voltage of 250 keV.

An acrylic foam tape (PT1100, available from 3M Company) was used to evaluate the release and readhesion to stainless steel after a three day dwell at room temperature (3d-RT) and a three day dwell at 70° C. (3d-HT). The adhesive was an acrylic/rubber blend. Release and readhesion was tested using a dry lamination process. First, the liner on the commercial PT1100 acrylic foam tape was removed and the release force recorded. Readhesion to stainless steel of this 'as provided" material was also measured, for comparison purposes.

Next, the liner was removed from additional samples the PT1100 acrylic foam tape and the exposed adhesive was dry laminated to the e-beam cured silicone surfaces of the test samples. The samples were conditioned and the release force and readhesion force were measured. The results are summarized in Table 2.

TABLE 2

Release and readhesion results for e-beam cured, silanol functional silicones.

| | | Dose | 3d-RT (gm/2.54 cm) | | 3d-HT (gm/2.54 cm) | |
|---|---|---|---|---|---|---|
| Ex. | Adh. | (Mrad) | Release | Readhesion | Release | Readhesion |
| CE-1 | PT1000 | (*) | 332 | 6760 | 472 | 6990 |
| 8 | PT1000 | 12 | 306 | 3930 | 571 | 5630 |
| 9 | PT1000 | 16 | 181 | 5940 | 415 | 7440 |
| 10 | PT1000 | 19 | 106 | 9590 | 357 | 7920 |

(*) standard product liner, not an e-beam cured silicone.

The following samples were prepared by electron beam curing an alkoxy terminated functional silicone fluid. Trimethyl siloxy terminated polydimethyl siloxane (DMS-T21, 100 cSt, from Gelest) was coated with a flat, stiff blade to a coat weight of 0.70 gram/square meter on a 115 micron (4.5 mil) thick polyethylene liner, which had been nitrogen corona treated at 0.71 Joule per square centimeter. The coated samples were electron beam cured in an inert atmosphere (less than 50 ppm oxygen) using an acceleration voltage of 250 keV.

An acrylic foam tape (EX4011, available from 3M Company) was used to evaluate the release and readhesion to stainless steel after a seven day dwell at room temperature (7d-RT). The adhesive was an rubber/acrylic blend. Release and readhesion was tested using a dry lamination process. First, the liner on the commercial EX4011 acrylic foam tape was removed and the release force recorded. Readhesion to stainless steel of this 'as provided" material was also measured, for comparison purposes.

Next, the liner was removed from additional samples the EX4011 acrylic foam tape and the exposed adhesive was dry laminated to the e-beam cured silicone surfaces of the test samples. The samples were conditioned and the release force and readhesion force were measured. The results are summarized in Table 3.

TABLE 3

Release and readhesion results for e-beam cured, functional silicones.

| | | | 7d-RT (gm/2.54 cm) | |
|---|---|---|---|---|
| Ex. | Adh. | Dose (Mrad) | Release | Readhesion |
| CE-2 | EX4011 | (*) | 304 | 4270 |
| 11 | EX4011 | 250 kev | 244 | 1670 |

(*) standard product liner, not an e-beam cured silicone.

Although there was some cure of this trimethyl siloxy terminated polydimethyl siloxane, the low readhesion values indicate an under cured system.

The EX4011 acrylic foam tape adhesive was also dry laminated to a sample of silanol terminated polydimethyl siloxane (DMS-S42, 18,000 cSt, from Gelest) that was coated with a flat, stiff blade to a coat weight of 1.8 gram/square meter on a 115 micron (4.5 mil) thick polyethylene liner, which had been nitrogen corona treated at 0.71 Joule per square centimeter. The coated samples were electron beam cured in an inert atmosphere (less than 50 ppm oxygen) using an acceleration voltage of 250 keV and 16 Mrads. The 7d-RT release was 221 g/2.54 cm. The 7d-RT readhesion was 4560 gm/2.54 cm.

Other Functional Groups.

The following comparative example was prepared by attempting to electron beam curing a hydride functional silicone fluid. Hydride terminated polydimethyl siloxane (DMS-H25, 500 cSt, from Gelest) was coated with a flat, stiff blade to a coat a 115 micron (4.5 mil) thick polyethylene liner, which had been nitrogen corona treated at 0.71 Joule per square centimeter. The coated samples were exposed to electron beam irradiation in an inert atmosphere (less than 50 ppm oxygen) using an acceleration voltage of 250 keV and dose of 16 Mrad. The sample did not cure.

The following comparative example was prepared by attempting to electron beam curing a vinyl functional silicone fluid. Vinyl terminated polydimethyl siloxane (DMS-V42, 20,000 cSt, from Gelest) was coated with a flat, stiff blade to a coat a 115 micron (4.5 mil) thick polyethylene liner, which had been nitrogen corona treated at 0.71 Joule per square centimeter. The coated samples were exposed to electron beam irradiation in an inert atmosphere (less than 50 ppm oxygen) using an acceleration voltage of 250 keV and dose of 16 Mrad. The sample cured but did not anchor to the underlying polyethylene liner. The cured siloxane could be rubbed off the liner.

The following comparative example was prepared by attempting to electron beam curing a carboxyalkyl functional silicone fluid. Carboxyalkyl terminated polydimethyl siloxane (DMS-B31, 800-1200 cSt, from Gelest) was coated with a flat, stiff blade to a coat a 115 micron (4.5 mil) thick polyethylene liner, which had been nitrogen corona treated at 0.71 Joule per square centimeter. The coated samples were exposed to electron beam irradiation in an inert atmosphere (less than 50 ppm oxygen) using an acceleration voltage of 250 keV and dose of 16 Mrad. The sample did not cure.

Low kinematic viscosity sample. The following comparative example was prepared by attempting to electron beam curing a low viscosity, low molecular weight silanol functional silicone fluid. Silanol terminated polydimethyl siloxane (DMS-S12, 20 cSt, from Gelest) was coated with a flat, stiff blade to a coat a 115 micron (4.5 mil) thick polyethylene liner, which had been nitrogen corona treated at 0.71 Joule per square centimeter. The coated samples were exposed to electron beam irradiation in an inert atmosphere (less than 50 ppm oxygen) using an acceleration voltage of 250 keV and dose of 16 Mrad. The sample did not cure.

An exemplary release liner according to some embodiments of the present disclosure is illustrated in FIG. 1. Release liner 100 comprises substrate 120 with e-beam cured silicone release coating 130 associated with one major surface of substrate 120. In some embodiments, a second e-beam cured release layer may be associated with the second major surface of the substrate, opposite the first e-beam cured silicone release coating.

Various modifications and alterations of this invention will become apparent to those skilled in the art without departing from the scope and spirit of this invention.

What is claimed is:

1. A method of making a silicone release layer comprising: applying a composition comprising one or more polysiloxane materials on a substrate and electron beam curing the composition to crosslink the polysiloxane materials, wherein the polysiloxane materials comprise nonfunctional polysiloxanes, wherein each nonfunctional polysiloxane is a polysiloxane fluid having a kinematic viscosity at 25° C. no greater than 50,000 centistokes, wherein the composition is substantially free of catalysts and initiators.

2. The method of claim 1, wherein the polysiloxane material consists essentially of one or more polysiloxane fluids having a kinematic viscosity at 25° C. of no greater than 50,000 centistokes.

3. The method of claim 1, wherein the polysiloxane material comprises a poly dimethylsiloxane.

4. The method according to claim 1, wherein all polysiloxane materials in the composition are nonfunctional polysiloxanes.

5. The method of claim 4, wherein each nonfunctional polysiloxane is a polysiloxane fluid having a kinematic viscosity at 25° C. no greater than 50,000 centistokes.

6. The method according to claim 1, wherein the composition is substantially free of catalysts and initiators.

7. The method according to claim 1, wherein the composition comprises no greater than 5 wt. % solvent.

8. The method of claim 1, wherein the polysiloxane materials further comprises at least one of silanol terminated polysiloxanes, alkoxy terminated polysiloxane, and combinations thereof.

* * * * *

UNITED STATES PATENT AND TRADEMARK OFFICE
CERTIFICATE OF CORRECTION

| | | |
|---|---|---|
| PATENT NO. | : 8,822,559 B2 | Page 1 of 1 |
| APPLICATION NO. | : 13/126365 | |
| DATED | : September 2, 2014 | |
| INVENTOR(S) | : Panu Zoller | |

It is certified that error appears in the above-identified patent and that said Letters Patent is hereby corrected as shown below:

Title Page:

Item 73 (Assignee)
Line 1, delete "3D" and insert -- 3M --

In the Specification:

Column 4
Line 16 (approx.), delete "is" and insert -- in --

Line 67, delete "cSt" and insert -- cSt. --

Column 6
Line 41 (approx.), delete "'as" and insert -- "as --

Column 7
Line 13 (approx.), delete "'as" and insert -- "as --

Line 31 (approx.), delete "kev" and insert -- keV --

Signed and Sealed this
Eleventh Day of August, 2015

Michelle K. Lee
*Director of the United States Patent and Trademark Office*